US012478466B2

(12) United States Patent
Dykes et al.

(10) Patent No.: US 12,478,466 B2
(45) Date of Patent: Nov. 25, 2025

(54) INTRAOCULAR LENS PUNCH

(71) Applicants: International Science & Technology, LP, The Woodlands, TX (US); John Morgan Micheletti, Sugar Land, TX (US)

(72) Inventors: Ronald Dykes, The Woodlands, TX (US); John Morgan Micheletti, Sugar Land, TX (US)

( * ) Notice: Subject to any disclaimer, the term of this patent is extended or adjusted under 35 U.S.C. 154(b) by 790 days.

(21) Appl. No.: 17/732,415

(22) Filed: Apr. 28, 2022

(65) Prior Publication Data

US 2022/0346944 A1 Nov. 3, 2022

Related U.S. Application Data

(63) Continuation of application No. 29/788,806, filed on Jul. 29, 2021, now Pat. No. Des. 995,778.

(60) Provisional application No. 63/181,946, filed on Apr. 29, 2021.

(51) Int. Cl.
*A61F 2/16* (2006.01)
*A61F 2/14* (2006.01)
*B26F 1/34* (2006.01)

(52) U.S. Cl.
CPC .............. *A61F 2/1664* (2013.01); *A61F 2/15* (2015.04); *B26F 1/34* (2013.01); *A61F 2002/1681* (2013.01); *A61F 2240/001* (2013.01)

(58) Field of Classification Search
CPC ....... A61F 2/15; A61F 9/007; A61B 17/32053
See application file for complete search history.

(56) References Cited

U.S. PATENT DOCUMENTS 4,190,050 A 2/1980 Bailey
4,336,805 A 6/1982 Smirmaul
4,409,690 A * 10/1983 Gess ......................... A61F 2/15 623/6.43
4,423,728 A 1/1984 Lieberman
4,494,254 A * 1/1985 Lopez ..................... A61L 27/16 2/900
4,504,981 A * 3/1985 Walman .................... A61F 2/16 623/6.54
4,750,491 A 6/1988 Kaufman et al.
(Continued)

FOREIGN PATENT DOCUMENTS

RU 2665182 C1 * 8/2018
RU 2681108 C1 * 3/2019

OTHER PUBLICATIONS

Translation of RU-2665182-C1 (Year: 2018).*
Translation of RU-2681108-C1 (Year: 2019).*

*Primary Examiner* — Melanie R Tyson
*Assistant Examiner* — Paris Marie Blass
(74) *Attorney, Agent, or Firm* — Bradley Arant Boult Cummings LLP; Henry L. Ehrlich

(57) ABSTRACT

An intraocular lens (IOL) punch includes a handpiece having an opening at a first end, a jaw comprising a first leg and a second leg joined at a first rod end of a rod, the rod extending into the opening and moveable relative to the handpiece to operate the jaw between an open position and a closed position, and a post attached to the first leg and extending toward the second leg, wherein in the open position there is a gap between the post and the second leg and in the closed position the post extends to the second leg closing the gap.

20 Claims, 5 Drawing Sheets

(56) References Cited

U.S. PATENT DOCUMENTS

| | | | | | |
|---|---|---|---|---|---|
| 4,750,904 | A * | 6/1988 | Price, Jr. | A61F 2/1608 623/6.51 |
| 4,763,651 | A | 8/1988 | Kaufman et al. | |
| 4,796,623 | A | 1/1989 | Krasner et al. | |
| 5,084,059 | A | 1/1992 | Metzger | |
| 5,269,795 | A | 12/1993 | Arnott | |
| 5,290,301 | A | 3/1994 | Lieberman | |
| 5,480,426 | A * | 1/1996 | Chu | A61F 2/1608 623/6.55 |
| 5,531,756 | A * | 7/1996 | Larose | A61B 17/1608 606/174 |
| 5,632,757 | A | 5/1997 | Arnott | |
| 6,582,445 | B1 | 6/2003 | Koons | |
| 9,744,581 | B2 * | 8/2017 | Bullard | B26F 1/36 |
| D819,817 | S | 6/2018 | Weston et al. | |
| 10,080,685 | B2 | 9/2018 | Weston et al. | |
| 10,149,785 | B2 | 12/2018 | Thistle | |
| 2004/0122461 | A1 * | 6/2004 | McGuire | A61B 17/1608 606/184 |
| 2012/0022525 | A1 * | 1/2012 | Dietz | A61B 18/1445 606/45 |
| 2014/0046125 | A1 * | 2/2014 | Gillespie, Jr. | A61B 17/3478 600/31 |
| 2014/0358155 | A1 * | 12/2014 | DeBoer | A61F 2/1662 606/107 |
| 2016/0022488 | A1 * | 1/2016 | Dimmig | A61F 2/1664 606/107 |
| 2016/0067096 | A1 | 3/2016 | Weston et al. | |
| 2016/0151151 | A1 * | 6/2016 | Kleinman | A61F 2/14 623/6.12 |
| 2018/0271704 | A1 * | 9/2018 | Lifshitz | A61F 9/00754 |
| 2018/0368971 | A1 * | 12/2018 | Zacher | A61F 2/16 |

* cited by examiner

INTRAOCULAR LENS PUNCH

BACKGROUND

This section provides background information to facilitate a better understanding of the various aspects of the disclosure. It should be understood that the statements in this section of this document are to be read in this light, and not as admissions of prior art.

Intraocular (single-piece or three-piece) lenses are used in ophthalmic cataract surgeries to repair or replace the lens of the eye to resolve vision loss. Occasionally, these intraocular lenses can dislocate either partially or entirely. Intraocular lens dislocation rate has been reported to be up to three percent. While some options, like the Yamane technique, exist for three-piece intraocular lenses, three-piece intraocular lenses only make up a very small proportion of implanted intraocular lenses.

Currently, there are few options available to rescue or reposition single piece intraocular lenses without significant surgical skills in a complex and high-risk surgery. Many surgeons opt to explant the dislocated lens and perform the insertion of a completely new intraocular lens. The existing methods pose an increased risk to the patient as well as cost to both the patient and surgery center as a new lens must be procured to implant and patient recovery from such procedures is typically longer.

SUMMARY

An exemplary intraocular lens (IOL) punch includes a handpiece having an opening at a first end, a jaw comprising a first leg and a second leg joined at a first rod end of a rod, the rod extending into the opening and moveable relative to the handpiece to operate the jaw between an open position and a closed position, and a post attached to the first leg and extending toward the second leg, wherein in the open position there is a gap between the post and the second leg and in the closed position the post extends to the second leg closing the gap.

An exemplary method includes creating a hole in an intraocular lens (IOL) and securing the IOL to an eye with suture passing through the hole.

Another exemplary method includes using a punch to create a hole in an IOL, the punch comprising a jaw having a first leg and a second leg joined at a first rod end of a rod, the rod extending into an opening in a handpiece and moveable relative to the handpiece to operate the jaw between an open position and a closed position, and a post attached to the first leg and extending toward the second leg, wherein in the open position there is a gap between the post and the second leg and in the closed position the post extends to the second leg closing the gap, placing a portion of the IOL in the gap, moving the jaw to the closed position thereby creating the hole in the IOL, opening the jaw, and removing the IOL from the gap.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion. As will be understood by those skilled in the art with the benefit of this disclosure, elements and arrangements of the various figures can be used together and in configurations not specifically illustrated without departing from the scope of this disclosure.

DETAILED DESCRIPTION

Figure 1:
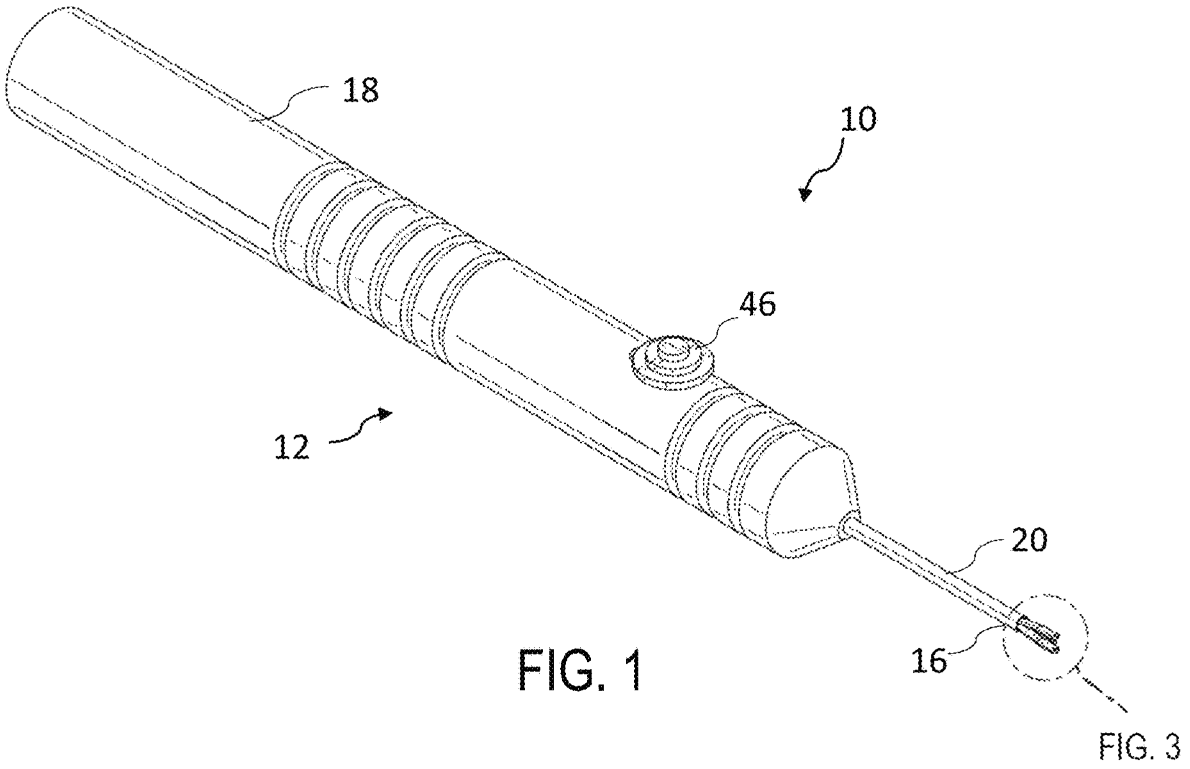
FIG. 1 is a perspective view of an exemplary intraocular lens (IOL) punch.
Figure 2:
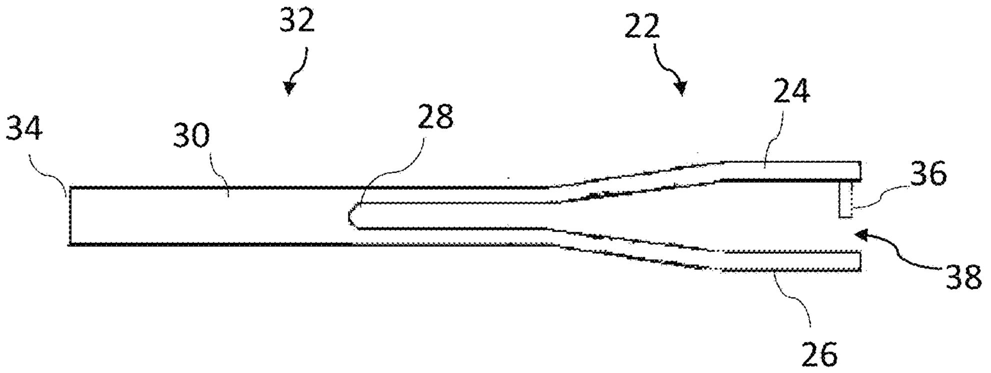
FIG. 2 illustrates an exemplary jaw of an IOL punch.
Figure 3:
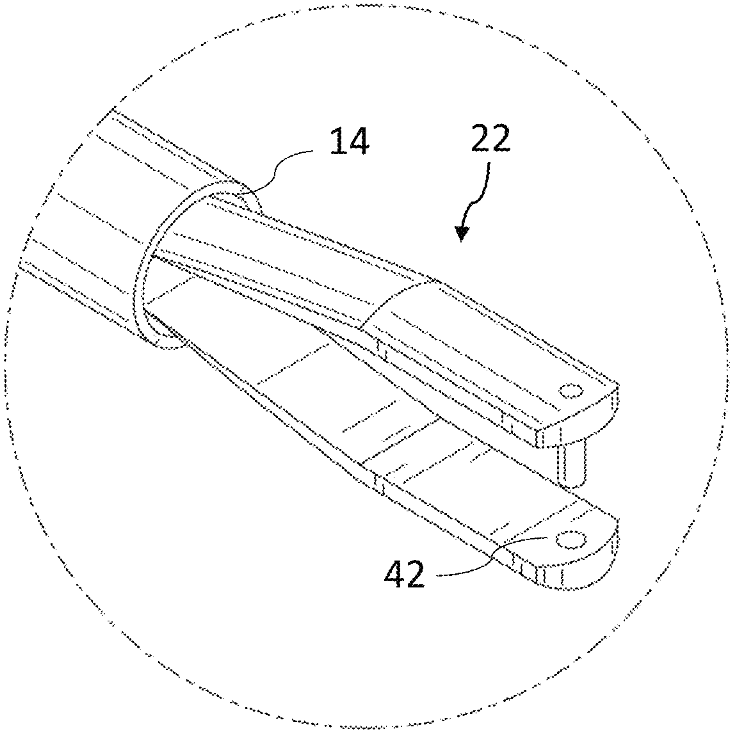
FIG. 3 is an expanded view of the jaw of FIG. 1.

It is to be understood that the following disclosure provides many different embodiments, or examples, for implementing different features of various illustrative embodiments. Specific examples of components and arrangements are described below to simplify the disclosure. These are, of course, merely examples and are not intended to be limiting. For example, a figure may illustrate an exemplary embodiment with multiple features or combinations of features that are not required in one or more other embodiments and thus a figure may disclose one or more embodiments that have fewer features or a different combination of features than the illustrated embodiment. Embodiments may include some but not all the features illustrated in a figure and some embodiments may combine features illustrated in one figure with features illustrated in another figure. Therefore, combinations of features disclosed in the following detailed description may not be necessary to practice the teachings in the broadest sense and are instead merely to describe particularly representative examples. In addition, the disclosure may repeat reference numerals and/or letters in the various examples. This repetition is for the purpose of simplicity and clarity and does not itself dictate a relationship between the various embodiments and/or configurations discussed.

Although relative terms such as "outer," "inner," "upper," "lower," and similar terms have been used herein to describe a spatial relationship of one element to another, it is understood that these terms are intended to encompass different orientations of the various elements and components in addition to the orientation depicted in the figures. Additionally, as used herein, the term "substantially," "about," "generally," and similar terms are used as terms of approximation and not a terms of degrees, and are intended to account for the inherent deviations in measured and calculated values that would be recognized by a person of skill in the art. Furthermore, as used herein, the terms "connect," "connection," "connected," "in connection with," and "connecting" may be used to mean in direct connection with or in connection with via one or more elements. Similarly, the terms "couple," "coupling," and "coupled" may be used to mean directly coupled or coupled via one or more elements.

Discloses are intraocular lens (IOL) punches and methods of using an IOL punch to secure a dislocated IOL in an eye. The IOL punches include a jaw that is operable between an open position and a closed position. The jaw operable to create a hole in an IOL lens when operated to the closed position.

Figure 4:
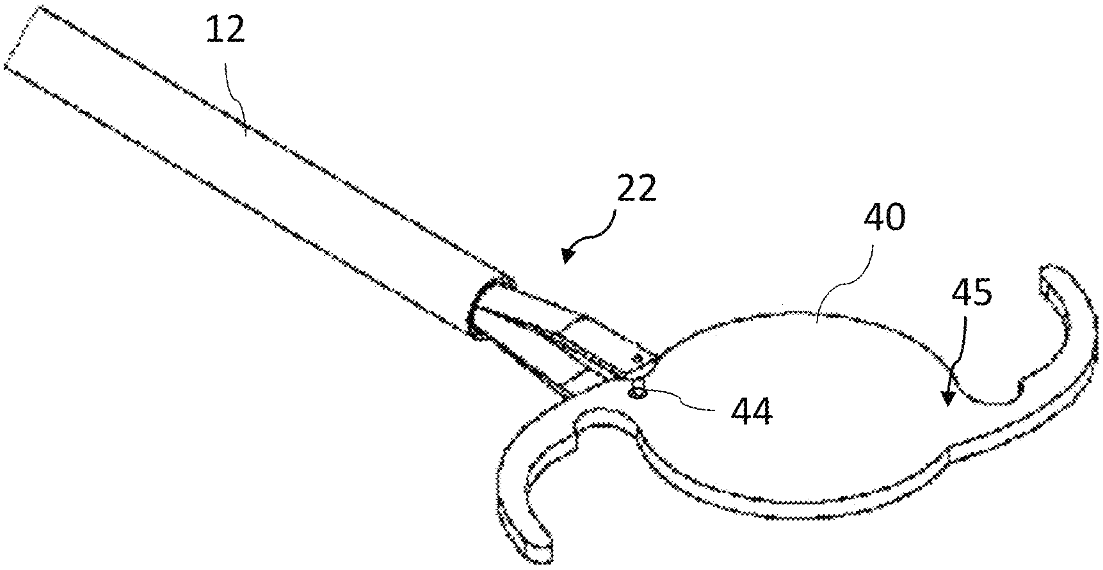
FIG. 4 illustrates an exemplary IOL punch positioned to create a hole through an IOL.

FIGS. 1-4 illustrate aspects of an exemplary intraocular lens (IOL) punch, or trephine, generally designated with the numeral 10. IOL punch 10 includes a handpiece 12 having an opening 14 at a first end 16. First end 16 may be referred to as the forward end that will face an eye during use of the IOL punch. In the illustrated example, handpiece 12 includes a body 18 and a linear tube or sleeve 20 extending axially with the body. IOL punch 10 includes a jaw 22 having a first leg 24 and a second leg 26 joined at a first end 28 of a rod 30. Jaw 22 and rod 30 are generally referred to as an insert 32. The second end 34 of rod 30 and rod 30 are positioned inside of handpiece 12. Insert 32 is movable relative to handpiece 12 to operate jaw 22 between an open position, e.g., FIG. 3, and a closed position. A post 36 is attached to first leg 24 and extends toward second leg 26. In the open position there is a gap 38 between the post and the second leg such that an IOL 40, see e.g., FIG. 4, can be positioned in gap 38. In the closed position, post 36 extend to second leg 26 closing gap 38. Second leg 26 may have an aperture 42 into which post 36 extends when the jaw is in the closed position. Post 36 may be solid or tubular. When jaw 22 is closed on an IOL 40, post 36 forms a hole 44 through the IOL. In FIG. 4, hole 44 is formed through the haptic optic junction 45.

IOL punch includes an actuator 46 coupled with handpiece 12 and rod 30 operable to move the rod relative to the handpiece. For example, the actuator may move the rod relative to a stationary handpiece or move the handpiece relative to the stationary rod. As the jaw is moved inside the handpiece, the legs are urged toward each other closing the jaw.

Figure 5A:
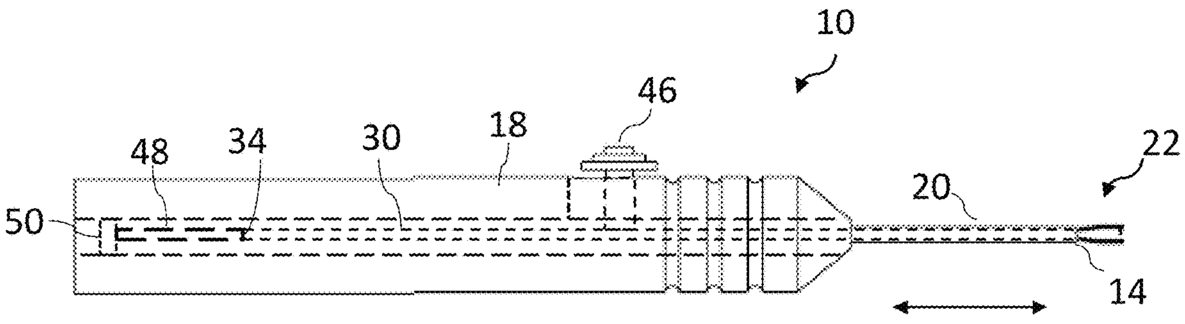
FIG. 5A is a schematic illustration of an exemplary IOL punch and actuating system.
Figure 5B:
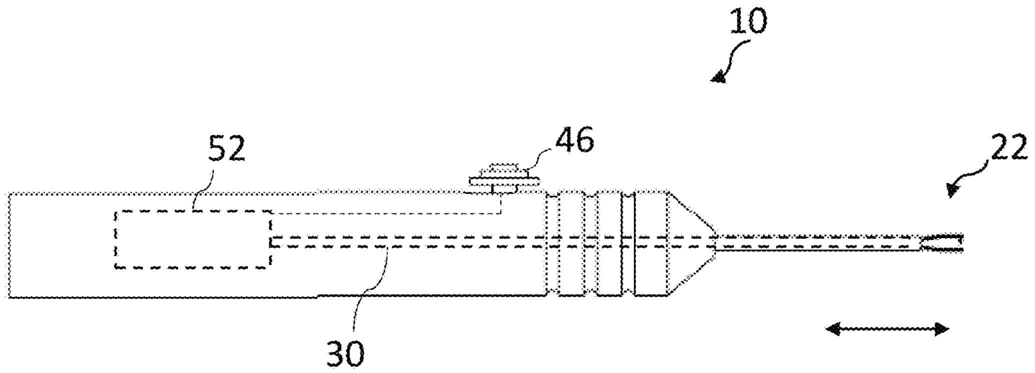
FIG. 5B is a schematic illustration of an exemplary IOL punch and actuating system.

FIGS. 5A and 5B illustrate exemplary IOL punches 10 and actuating systems. In FIG. 5A, actuator 46 is a for example a handle connected to the rod 30 whereby movement of actuator 46 axially moves rod 30 relative to the handpiece. Second end 34 of rod 30 is positioned inside of the handpiece, for example in body 18, and jaw 22 is located proximate opening 14. In the jaw open position, jaw 22 is located outside of opening 14. In the closed position, jaw 22 may be fully retracted inside handpiece 12, e.g., sleeve 20, or retracted a sufficient distance to close jaw 22. In the illustrated exemplary embodiment, a biasing member 48 is in contact with rod 30 and the handpiece, for example at stop 50, and biases rod 30 and jaw 22 to a default position. For example, the default position may be jaw open or jaw closed.

FIG. 5B illustrates a motorized actuating system. In this example, actuator 46 includes an electric motor 52. Actuator 46 is a switch to operate motor 52 and to cause jaw 22 to move toward the handpiece to actuate jaw 22 to the closed position.

Figure 6:
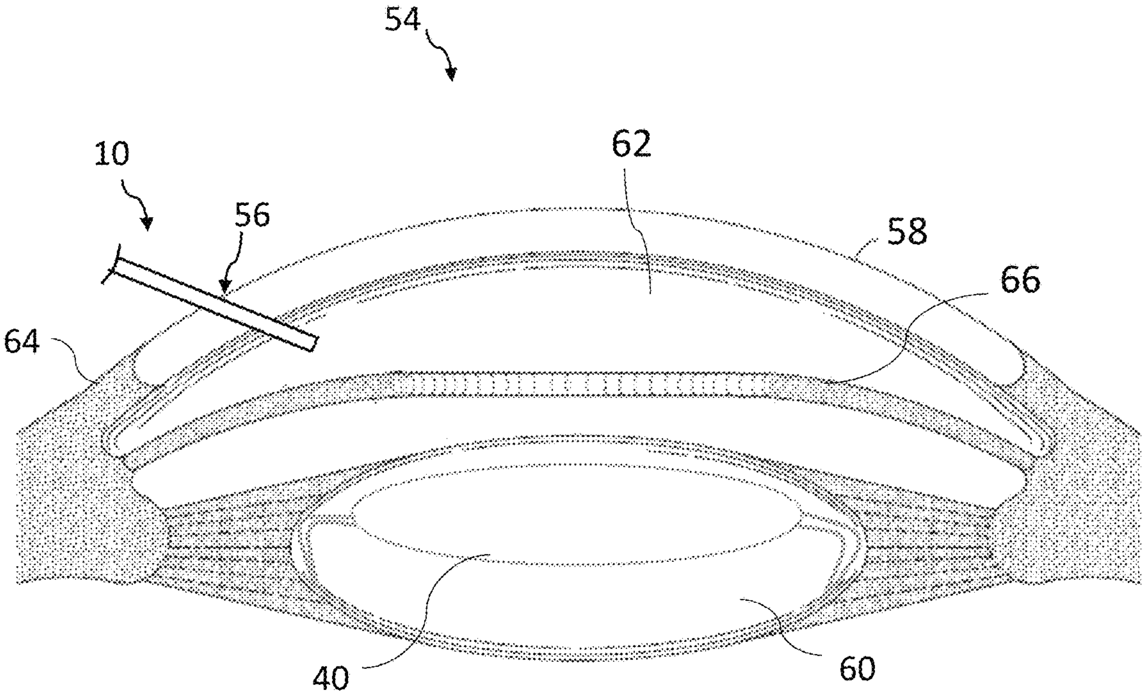
FIG. 6 schematically illustrates an IOL punch in use.

FIG. 6 schematically illustrates an IOL punch 10 in use with an eye 54. IOL punch 10, e.g., the sleeve, is inserted through an incision 56 in the cornea 58. IOL 40 is shown located in the posterior lens chamber 60, however, it could be located in the anterior lens chamber 62

Figure 7:
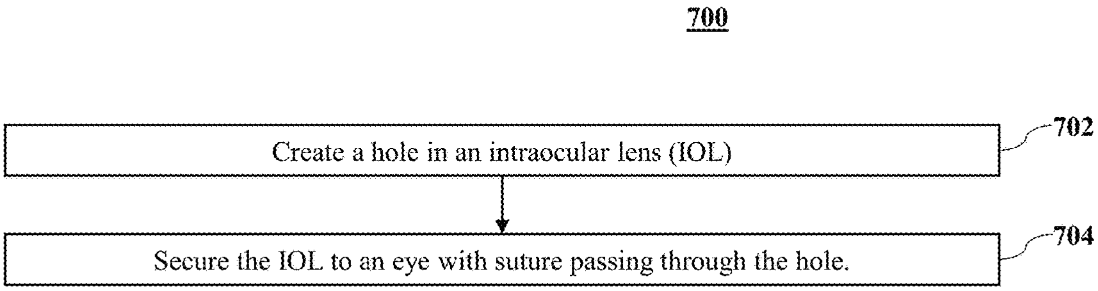
FIG. 7 is a block diagram of an exemplary method for repositioning a disclosed IOL in an eye.

Exemplary methods of securing a dislocated IOL 40 in an eye are described with reference to FIGS. 1-4, 5A, 5B, and 6-8. With reference to FIG. 7, at block 702 a hole is formed in an IOL that may be located in an eye. The IOL is correctly positioned in the eye. At block 704, the IOL is secured in the proper position by a suture passing the hole in the IOL. The IOL may be sutured for example to the sclera 64 or iris 66.

Figure 8:
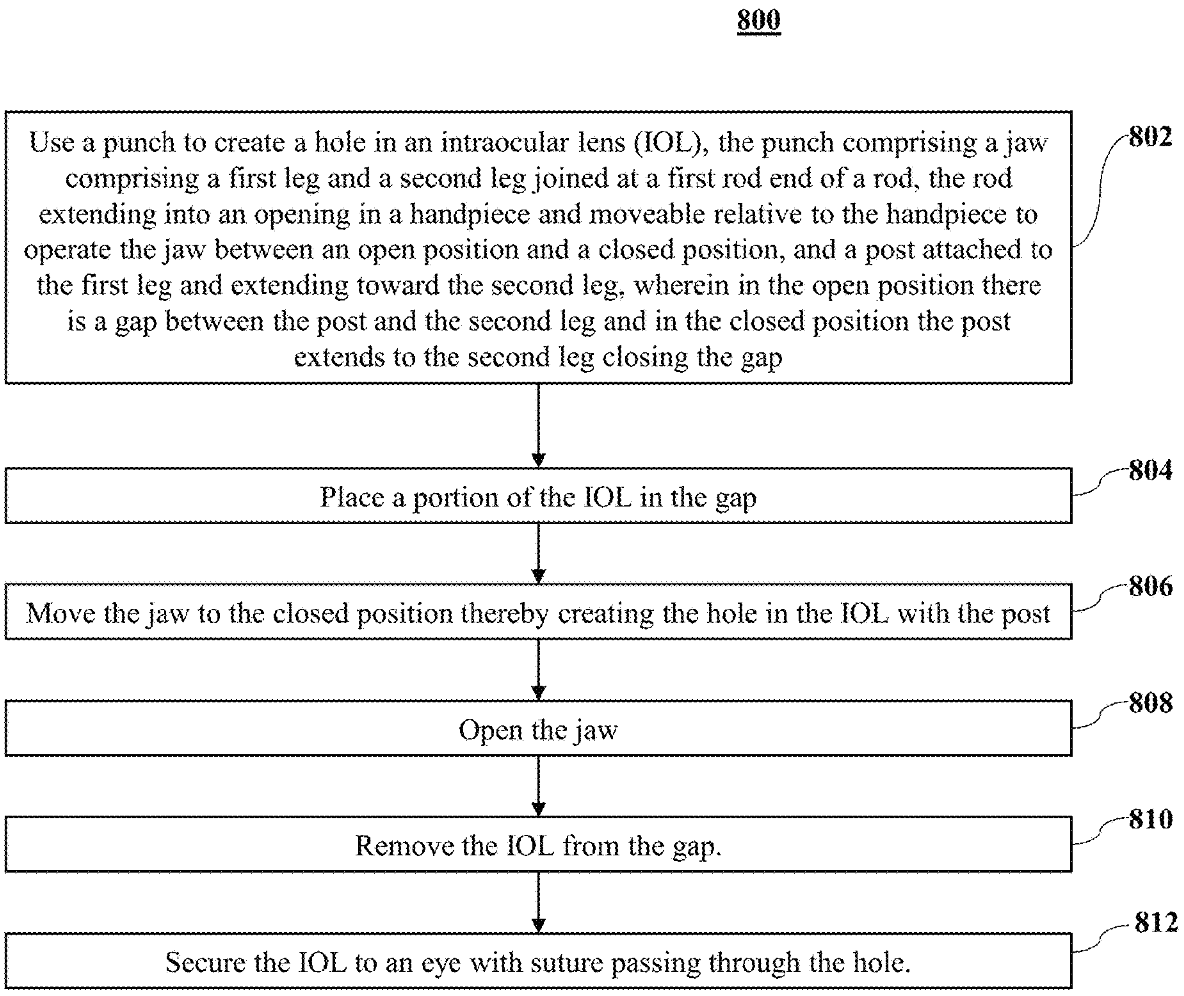
FIG. 8 is a block diagram of another exemplary method for repositioning a disclosed IOL in an eye.

With reference in particular to FIG. 8, at block 802 an IOL punch is used to create a hole in an IOL. For example, the IOL may be dislocated in an eye. A jaw of the IOL punch is inserted into the eye through a corneal incision. At block 804, a portion of the IOL is positioned in the gap of an open jaw. At block 806, the jaw is actuated to the closed position creating a hole in the portion of the IOL that is positioned in the gap. At blocks 808 and 810, the jaw is opened and the IOL is removed from the jaw gap. At block 812, the IOL is secured in the proper position in the eye with a suture passing through the hole created in the IOL with the punch.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A method comprising:

using a punch to create a hole in an intraocular lens (IOL), the punch comprising a jaw having a first leg and a second leg joined at a first rod end of a rod, the rod extending into an opening in a handpiece and moveable relative to the handpiece to operate the jaw between an open position and a closed position, and a post attached to the first leg and extending toward the second leg, wherein in the open position there is a gap between the post and the second leg and in the closed position the post extends to the second leg closing the gap;

placing a portion of the IOL in the gap;

moving the jaw to the closed position thereby creating the hole in the IOL;

opening the jaw; and removing the IOL from the gap.

2. The method of claim 1, further comprising securing the IOL in an eye with a suture passing through the hole.

3. The method of claim 1, wherein the moving the jaw to the closed position comprises moving the jaw into the opening of the handpiece.

4. The method of claim 1, wherein the moving the jaw to the closed position comprises manually moving the jaw toward the handpiece.

5. The method of claim 1, comprising positioning the jaw through a corneal incision in an eye; and creating the hole with the IOL located in the eye.

6. The method of claim 5, further comprising securing the IOL in the eye with a suture passing through the hole.

7. The method of claim 6, wherein the IOL is secured to a sclera with the suture.

8. The method of claim 5, wherein the hole is created in a haptic-optic junction of the IOL.

9. The method of claim 8, wherein the IOL is secured to a sclera with the suture.

10. The method of claim 8, wherein the moving the jaw to the closed position comprises manually moving the jaw toward the handpiece.

11. The method of claim 1, further comprising an actuator coupled with the handpiece and the rod, the actuator operable to move the rod relative to the handpiece.

12. The method of claim 11, wherein the actuator is an electric motor.

13. The method of claim 11, wherein the actuator is a handle manually operable to move the rod.

14. The method of claim 1, wherein the second leg comprises an aperture and the post extends into the aperture when the jaw is in the closed position.

15. The method of claim 1, further comprising an actuator coupled with the handpiece and the rod, the actuator operable to move the rod relative to the handpiece; and the second leg comprising an aperture, wherein the post extends into the aperture when the jaw is in the closed position.

16. The method of claim 15, further comprising:

positioning the jaw through a corneal incision in an eye; and creating the hole with the IOL located in the eye.

17. The method of claim 16, further comprising securing the IOL in the eye with a suture passing through the hole.

18. The method of claim 17, wherein the IOL is secured to a sclera with the suture.

19. The method of claim 16, wherein the hole is created in a haptic-optic junction of the IOL.

20. The method of claim 19, wherein the IOL is secured to a sclera with the suture.

* * * * *